US008880159B2

(12) United States Patent
Tereshchenko et al.

(10) Patent No.: US 8,880,159 B2
(45) Date of Patent: Nov. 4, 2014

(54) METHODS FOR DETERMINING RISK OF VENTRICULAR ARRHYTHMIA

(75) Inventors: Larisa Tereshchenko, Baltimore, MD (US); Ronald Berger, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 366 days.

(21) Appl. No.: 13/082,366

(22) Filed: Apr. 7, 2011

(65) Prior Publication Data

US 2011/0251504 A1 Oct. 13, 2011

Related U.S. Application Data

(60) Provisional application No. 61/321,591, filed on Apr. 7, 2010, provisional application No. 61/325,901, filed on Apr. 20, 2010, provisional application No. 61/355,285, filed on Jun. 16, 2010.

(51) Int. Cl.
| | |
|---|---|
| *A61B 5/04* | (2006.01) |
| *A61B 5/02* | (2006.01) |
| *A61B 5/0452* | (2006.01) |
| *A61B 5/0464* | (2006.01) |
| *A61B 5/046* | (2006.01) |

(52) U.S. Cl.
CPC ........... *A61B 5/04011* (2013.01); *A61B 5/0464* (2013.01); *A61B 5/046* (2013.01); *A61B 5/0452* (2013.01)
USPC ........... 600/512; 600/508; 600/509; 600/515; 600/516; 600/517; 600/518

(58) Field of Classification Search
USPC .......................... 600/508, 512, 515–518, 509
See application file for complete search history.

(56) References Cited

U.S. PATENT DOCUMENTS

| 5,520,191 | A | * | 5/1996 | Karlsson et al. | 600/515 |
|---|---|---|---|---|---|
| 7,512,439 | B1 | * | 3/2009 | Farazi | 600/509 |
| 2004/0092836 | A1 | * | 5/2004 | Ritscher et al. | 600/518 |

OTHER PUBLICATIONS

STEPS: Reducing Artifact on Electrocardiographs. (2008). Retrieved Feb. 6, 2013, from WelchAllyn website: http://www.welchallyn.com/documents/Cardiopulmonary/learningfiles/M5539WTP%20ReduceArtifact.pdf, p. 2.*
De Jaegere et al., "Intravascular ultrasound-guided optimized stent deployment. Immediate and 6 months clinical and angiographic results from the Multicenter Ultrasound Stenting in Coronaries Study (MUSIC Study)", *Eur. Heart J.*, 19(8):1214-23 (1998).
Kilgore et al., "Combined Direct Current and High Frequency Nerve Block for Elimination of the Onset Response", *31st Annual International Conference of the IEEE EMBS Minneapolis*, Minnesota, USA, Sep. 2-6, 2009.
Moss A.J., "MADIT-II and its implications", *Eur. Heart J.*, 24(1):16-8 (2003).
Roberts et al., "The defibrillation efficacy of high frequency alternating current sinusoidal waveforms in guinea pigs", *Pacing Clin. Electrophysiol.*, 26(2 Pt 1):599-604 (2003).

(Continued)

*Primary Examiner* — Niketa Patel
*Assistant Examiner* — William Levicky
(74) *Attorney, Agent, or Firm* — DLA Piper LLP (US)

(57) ABSTRACT

Methods and systems are disclosed for analyzing three dimensional orthogonal ECG measurements to assess patient risk of a subsequent cardiac event based on evaluation of cardiac vector values in view of risk factors defined by the invention.

22 Claims, 9 Drawing Sheets

(56) References Cited

OTHER PUBLICATIONS

Tanner J.A., "Reversible blocking of nerve conduction by alternating-current excitation", *Nature*, 195:712-3 (1962).

Zhang et al., "Mechanism of nerve conduction block induced by high-frequency biphasic electrical currents", *IEEE Trans Biomed Eng.*, 53(12 Pt 1):2445-54 (2006).

* cited by examiner

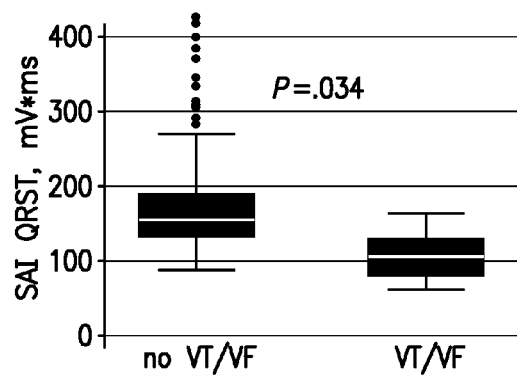 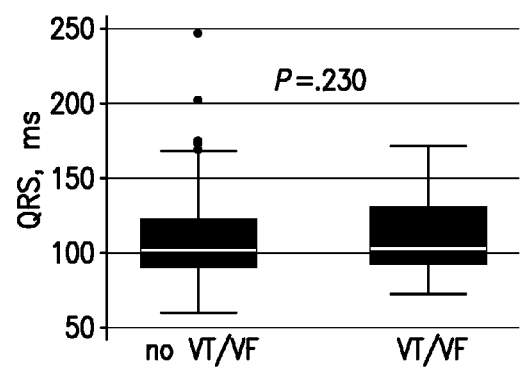
FIG. 8A  FIG. 8B

METHODS FOR DETERMINING RISK OF VENTRICULAR ARRHYTHMIA

RELATED APPLICATIONS

This application claims the benefit of U.S. Provisional Application Ser. No. 61/321,591, filed on Apr. 7, 2010, U.S. Provisional Application Ser. No. 61/325,901, filed on Apr. 20, 2010, and U.S. Provisional Application Ser. No. 61/355,285, filed on Jun. 16, 2010, the disclosures of which are hereby incorporated by reference in their entirety.

FIELD OF THE INVENTION

The present invention relates to the analysis of orthogonal echocardiogram (ECG) data to determine patient risk of experiencing a subsequent cardiac event such as ventricular tachychardia (VT), ventricular fibrillation (VF), or ventricular arrhythmia (VA), collectively a "cardiac event".

BACKGROUND OF THE INVENTION

Sudden cardiac arrest (SCA) due to ventricular arrhythmia (VA) can result in sudden cardiac death (SCD), SCA accounts for 50% of all death from cardiovascular causes and strikes 250,000-350,000 victims in the United States every year. Implantable cardioverter-defibrillators (ICDs) are the treatment of choice for patients at risk for SCA, effectively terminating ventricular tachychardia or ventricular fibrillation (VTNF). The risk for SCA is highest in patients with significantly depressed left ventricular systolic function (left ventricular ejection fraction LVEF≤35%), and the overwhelming majority of SCA cases occur in heart failure with preserved ejection fraction (HFpEF) patients. Moreover, depressed LVEF only identifies approximately one-third of all victims of SCD.

Vectorcardiography has proven to be a useful, but underutilized diagnostic tool, providing similar diagnostic information as the traditional 12-lead electrocardiogram (ECG). In certain cases, vectorcardiograms (VCGs) have been shown to be a more powerful diagnostic tool than the ECG, such as in diagnosing acute myocardial infarction in the presence of bundle branch blocks. However, it rarely used in a clinical setting, and has limitations in detecting VA. For example, it has been demonstrated through evaluation of human transmural three dimensional (3D) ventricular activation maps that interrogation of the terminal QRS-ST segment of cardiac cycle SAECG in VCG fails to detect the cardiac signals generated by the myocardium which are responsible for VA in 95% of cases.

There remains, therefore, a need for improved detection and prediction of cardiac events, especially in patients who have previously suffered such an event.

SUMMARY OF THE INVENTION

The present invention relates to the analysis of orthogonal echocardiogram (ECG) data to determine patient risk of experiencing a subsequent cardiac event such as ventricular tachychardia or ventricular fibrillation (VT/VF) or ventricular arrhythmia (VA). The ECG measurements are most preferably obtained through vectorcardiography and expressed as three lead, three-dimensional (3D) orthogonal ECG data.

In particular, the invention provides a method for evaluating an individual's risk of a subsequent cardiac event, the method comprising the invention is performed by (a) obtaining ECG measurements of a patient with ECG measuring equipment, (b) providing the obtained ECG measurements to ECG analysis equipment that that receives the ECG measurements, performs an ECG analysis, and that provides ECG analysis results in a user readable format, and assigning a cardiac event risk factor based upon the value of the at least one cardiac event risk factor.

In particularly preferred embodiments of the invention, the method is practiced by acquisition of 3D orthogonal ECG data in the subject, plotting QRS- and T-loops in three dimensions (3D), and evaluation of one or more cardiac vectors represented in the plot against risk factors for the occurrence of VA, wherein the cardiac vectors are selected from the group of vectors consisting of SAI QRST, R/T peak volume, spatial QRST angle, T-T' angles, R-R' angles, T-axes amplitudes, R-axes amplitudes, QRS loops areas, and T loops areas.

In a first method, the risk factor that is determined is the sum magnitude of the absolute QRST integral (SAI QRST). In a particularly preferred embodiment of this method, the sum magnitude of the absolute QRST integral is performed at a low frequency (10 Hz to 50 Hz band). Analysis of the SAI QRST data allows for determination of whether the subject's risk of a subsequent cardiac event is low, intermediate/moderate or high, where a SAI QRST of greater than about 145 mV*ms indicates a low risk, a SAI QRST of from about 70 mV*ms to about 145 mV*ms can be considered to indicate an intermediate risk and a SAI QRST of less than about 69 mV*ms can be considered to indicate a high risk.

In a further embodiment of this method, the SAI QRST is utilized to screen patients with structural heart disease for implantation of an ICD (intracardiac device).

In a second method, the risk factor that is determined is the ratio of the T peaks cloud volume to the R peaks cloud volume, wherein a R/T ratio of 0.125 or lesser is indicative of a high risk of a subsequent cardiac event.

In a third method, a determination of risk is further defined by detection of beat-to-beat variability in any of the cardiac vectors evaluated.

In one embodiment of the third method, the variability is detected as a variance (Var) in the spatial QRST angle of greater than 90 degrees over multiple beats. Such detection confirms or enhances a determination of high risk for a subsequent cardiac event.

In a further embodiment of the third method, the variability is detected as a root mean square successive difference (rMSSD) in the measured spatial QRS-T angle>12° between multiple beats. Such detection confirms or enhances a determination of high risk for a subsequent cardiac event.

In yet a further embodiment of the third method, the variability is detected as Var in the measured spatial T-T' angle>65° between multiple beats. Such detection confirms or enhances a determination of high risk for a subsequent cardiac event.

In yet a further embodiment of the third method, the variability is detected as a rMSSD in the measured spatial T-T' angle>10°. Such detection confirms or enhances a determination of high risk for a subsequent cardiac event.

In any one of the methods described above, the method can include a step of assigning a cardiac event risk factor of low, intermediate, or high based upon the value of the at least one cardiac event risk factor.

In any of the methods described above, the subject patient with respect to whom the methods of the invention are practiced has suffered at least one prior cardiac event, which may be a prior VT, VF or VA event, or other conditions indicative of cardiac disease (e.g., congestive heart failure, high blood pressure or ischemia).

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE DRAWINGS

Specific examples have been chosen for purposes of illustration and description, and are shown in the accompanying drawings, forming a part of the specification.

FIG. 8 is a box plot of baseline SAI QRST and QRS width in subjects with and without VT/VF at follow up. Median (horizontal line crossing the boxes) and interquartile range (IQR) of SAI QRST (A) and QRS width (B) is shown. Whiskers indicate adjacent values, defined as the most extreme values with 1.5 IQR of the nearer quartile.

DETAILED DESCRIPTION OF THE INVENTION

General Caveats

Figure 1:
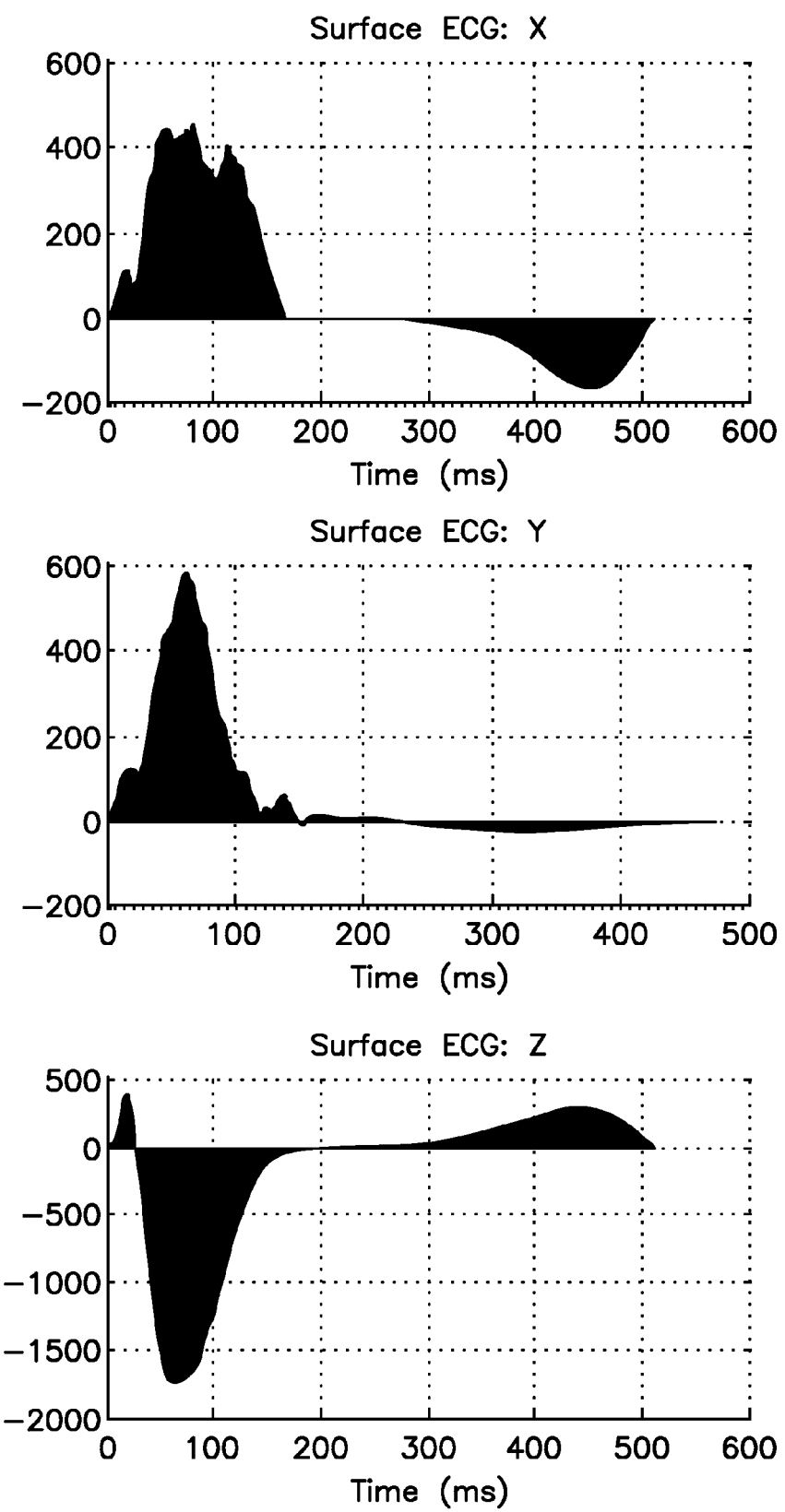
FIG. 1 illustrates the sum of the absolute areas under QRST curves for the X, Y and Z leads of an orthogonal ECG.

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments±50%, in some embodiments±20%, in some embodiments±10%, in some embodiments±5%, in some embodiments±1%, in some embodiments±0.5%, and in some embodiments±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

All publications and other printed materials referenced herein are incorporated herein by this reference.

Methods of the Invention

The invention provides systems and methods for analyzing electrocardiograph (ECG) measurements obtained from a patient using ECG equipment, which can include a surface ECG instrument or an intracardiac electrogram instrument, to determine a patient risk factor corresponding to the patient's level of risk of experiencing a subsequent cardiac event such as ventricular tachycardia or ventricular fibrillation (VTNF), or ventricular arrhythmia (VA).

In particular, the invention is performed by (a) obtaining ECG measurements of a patient with ECG measuring equipment, (b) providing the obtained ECG measurements to ECG analysis equipment that that receives the ECG measurements, performs an ECG analysis, and that provides ECG analysis results in a user readable format, and assigning a cardiac event risk factor based upon the value of the at least one cardiac event risk factor. The ECG analysis includes determining at least one cardiac event risk factor having a value, the at least one cardiac event risk factor being selected from the group consisting of a sum magnitude of the absolute QRST integral (SAI QRST), a ratio of R peaks cloud volume to T peaks cloud volume, a beat to beat variability of a spatial QRS-T angle, or a beat to beat variability of a spatial T-T' angle. In some examples, the ECG measurements can be obtained from a patient at rest during a rest time period, which can be any suitable time period, including but not limited to from about 2 minutes to about 10 minutes, including for example about 5 minutes.

A typical ECG tracing of the cardiac cycle (heartbeat) consists of a P wave, a QRS complex, a T wave, and a U wave (not always discernable on an ECG). For purposes of the invention, the principal focus is on the QRS complex and T wave segment of the sinus rhythm. For reference, the intervals and waves considered in ECG analysis are as follows:
P wave: precedes the R wave and corresponds to the sequential activation (depolarization) of the right and left atria;
PR interval: the period from the initiation of the P wave to the initiation of the R wave;
QRS complex: from the initiation to end of the R wave, including the Q and S segments—corresponds to right and left ventricular depolarization;
ST-segment: connection between the QRS complex and T wave which corresponds to ventricular repolarization;
T wave: follows the QRS complex and corresponds to repolarization (or recovery) of the ventricles;
U wave: follows the T wave and corresponds to post-depolarization in the ventricles;
RR interval: period from R wave to R wave and corresponds to the duration of ventricular cardiac cycle (an indicator of ventricular rate);
J-point: point where the QRS complex joins the ST segment;
Loop: a 3D representation of a wave; and,
Peak: the highest point in a loop or wave.
Waves, intervals, peaks, loops, loop volume may be manually or automatically calculated via a computer program in 3D ECG.

SAI QRST Risk Factor

The SAI QRST risk factor utilized in the present invention is based on analysis of baseline ECG data, plotting a QRST curve for the ECG data, and calculating the total sum of the absolute area under the QRST curve. In Example 1, discussed below, SAI QRST was determined for patients with structural heart disease having an ICD implanted for primary prevention of SCA, but those of ordinary skill in the art will appreciate that the measurement can be obtained in any mammal.

The QRST integral is a known metric that was conceived by Wilson et al., *Am Heart J*, 10:46-61 (1934), as the time integral of the heart vector, and the QRST is generally understood as expressing the heterogeneity of the AP morphology. Unlike the QRST integral, the SAI QRST disclosed herein can be calculated to adjust analysis to the requirements dictated by acquired filtered ECG signal characteristics, which gives the SAI QRST metric the added benefit of less dependence on a precise definition of the isoelectric baseline position.

The SAI QRST can be determined using either a surface ECG instrument or an intracardiac electrogram instrument. When the ECG measurement equipment includes an intracardiac electrogram instrument, the SAI QRST can be determined by plotting a QRST curve for the ECG measurements, and calculating the total sum of the absolute areas under the QRST curve. When the ECG measurement equipment includes a surface ECG instrument, and the ECG measurements are expressed as three lead orthogonal ECG data, whether or not the ECG measurements were obtained using three lead orthogonal ECG equipment. The SAI QRST for surface ECG measurements can be determined by plotting a QRST curve for each lead of the expressed three lead orthogonal ECG data, and calculating the total sum of the absolute areas under the QRST curve for each of the three leads.

Preferably, the SAI QRST determinations based on surface ECG instruments are obtained through use of three (3) lead orthogonal ECG measurement equipment instead of the conventional twelve (12) lead ECG equipment due to advantages provided by orthogonal ECG, which permits assessment of the whole heart cardiac vector. However, a standard 12-lead ECG provides spatial information about the heart's electrical activity in 3 approximately orthogonal directions, right and left; superior and inferior; and anterior and posterior, and can be converted or translated to be expressed as three lead orthogonal ECG data for use in the present invention.

Figure 2:
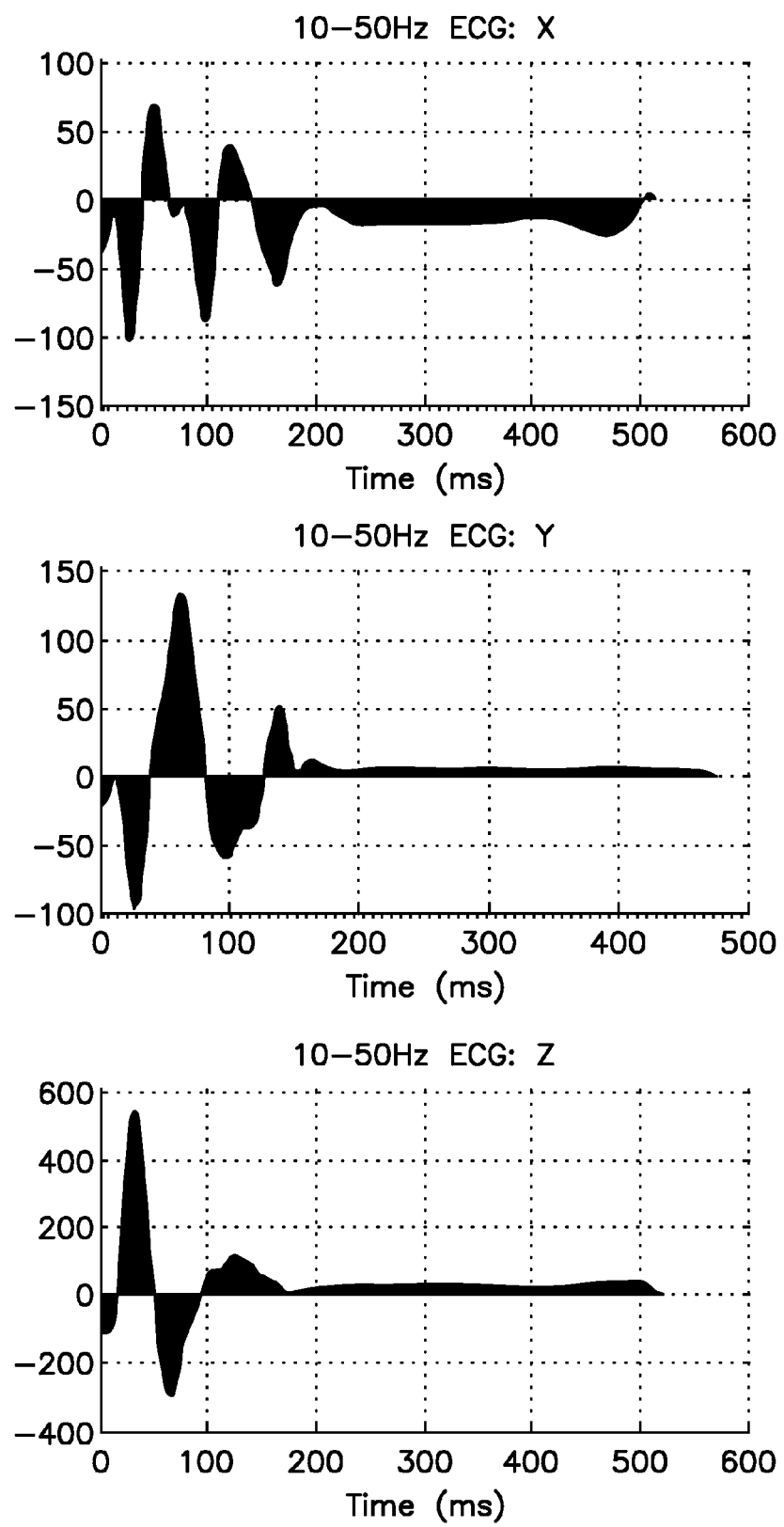
FIG. 2 illustrates the sum of the absolute areas under QRST curves for the X, Y and Z leads of a low frequency orthogonal ECG.

As discussed in Example 2 below, low frequency (10 Hz to 50 Hz band) SAI QRST measurement may improve the positive predictive value of the SAI QRST risk factor. A low frequency SAI QRST can be determined by calculating the SAI QRST of orthogonal ECG measurements taken in the 10 Hz to 50 Hz band. FIG. 2 illustrates one example of QRST curves that have been plotted for low frequency three (3) lead orthogonal ECG data in the 10 Hz to 50 Hz band.

Previous studies have shown the presence of low frequency signal through entire QRS (marker of intramural scar), whereas late potentials characterize presence of a particular subepicardial scar, and therefore could be frequently missing. In some examples, ECGs signals can be filtered to preserve the 10 Hz to 50 Hz band of three (3) lead orthogonal ECG data taken during a 5 minute rest period. One risk factor that can be calculated from ECG measurements that are filtered to preserve the 10 Hz to 50 Hz band of three (3) lead orthogonal ECG data taken during a patient rest period is the native QRST integral. The native QRST integral, $\int QT_{LF}$, can be calculated as mean algebraic sum of the areas under the low frequency QRST curve during the 5 minute rest period. When the native QRST is low, such as being below about zero, the risk factor for subsequent cardiac event can be considered to be high.

For example, in the study described in Example 1 below, the native QRST integral for ECG measurements in the low frequency band was significantly lower in patients with sustained VA and appropriate ICD therapies during follow-up (−335.3±1187.6 vs. 300.2±1378.9; t-test p=0.0003). Additionally, the SAI QRST risk factor of low frequency (10-50 Hz band) ECG signal can be calculated as mean arithmetic sum of the areas under QRST curves of each of the three leads.

One example of determining a SAI QRST from three lead orthogonal ECG data at low frequency is illustrated in FIG. 1. As illustrated, the SAI QRST can be determined by first plotting the QRST curve for each of the three leads (X, Y and Z) of the orthogonal ECG measurements obtained from a patient during an at rest time period of five (5) minutes. In alternative examples, the ECG measurements can be taken during any suitable at rest time period, including but not limited to time periods from about 10 seconds to about 10 minutes, including but not limited to 0.5, 1, 2, 3, 4, 5, 6, 7, 8, 9 or 10 minutes. The SAI QRST of the data in FIG. 1 can be determined by calculating the total sum of the absolute areas under the QRST curve, the absolute QRST integral, for each of the three leads. The absolute area under each QRST curve can be determined by adding the area under the QRST curve above baseline and the area below baseline. Accordingly, for the example illustrated in FIG. 1, the total sum of the absolute areas under the QRST curve for each of the three leads can be calculated by adding the absolute area under the QRST curve for the X lead with the absolute area under the QRST curve for the Y lead and the absolute area under the QRST curve for the Z lead.

Summation of absolute QRST integral of all three orthogonal ECG leads in the example of FIG. 1 to determine the SAI QRST can allow assessment of the magnitude of total cardiac electrical power and can eliminate bias of single lead axis position. A cardiac event risk factor is assigned to a patient based upon the value of the SAI QRST. Diminished total cardiac electrical power results in low SAI QRST. For example, generally, a SAI QRST of greater than about 145 mV*ms indicates a low risk of life-threatening ventricular tachyarrhythmias. Specifically, a SAI QRST of greater than about 145 mV*ms can be associated with a relatively low risk of arrhythmia in structural heart disease patients with implanted ICD for primary prevention of sudden cardiac death (see, Example 1 and FIGS. 7 and 8).

Conversely, the cardiac event risk factor for a SAI QRST of less than about 69 mV*ms can be high, and the cardiac event risk factor for a SAI QRST of from about 70 mV*ms to about 145 mV*ms can be considered intermediate.

Accordingly, the SAI QRST could be considered for screening patients with structural heart disease, and an indication against ICD implantation could be made for patients having a SAI QRST of greater than about 145 mV*ms. Substantial evidence supports the idea that patients with structural heart disease have some degree of risk of VT/VF during their lifetime. The strategy of identifying patients at low, rather than high, risk of VT/VF could maximize the benefit of primary prevention ICD, excluding those at low risk of VT/VF for whom the risk/benefit ratio of the ICD, including CHF progression is not favorable.

The SAI QRST methods of the invention have excellent predictive value as demonstrated in a receiver operating characteristic (ROC) Curve. A ROC curve is a generalization of the set of potential combinations of sensitivity and specificity possible for predictors. A ROC curve is a plot of the true positive rate (sensitivity) against the false positive rate (1-specificity) for the different possible cut-points of a diagnostic test. The Area under the Curve (AUC) represents an overall indication of the diagnostic accuracy of a ROC curve. AUC values closer to 1 indicate the screening measure reliably distinguishes among students with satisfactory and unsatisfactory reading performance, whereas values at 0.50 indicate the predictor is no better than chance.

For cardiac event prediction, biostatistical studies have identified the requirements for a good screening test and underscored the value of ROC analysis. Hazard ratios of most commonly employed predictors of SCD range from 2 to 6, which is insufficient for discrimination. In the prospective observational study of primary prevention ICD patients (PROSE-ICD) discussed in the Examples below, SAI QRST ROC analysis exhibited a large area under the curve (AUC) and hazard ratio range of 9-10, as well as high sensitivity and negative predictive value.

Ratio of T Peaks Cloud Volume to R Peaks Cloud Volume Risk Factor

The ratio of the T peaks cloud volume to the R peaks cloud volume is a risk factor that shows the relative volume of the T peaks cloud. Example 3 below discusses determination of the T peaks cloud volume to the R peaks cloud volume for patients based on analysis of baseline orthogonal ECG data of patients with structural heart disease having an ICD implanted for primary prevention of SCA. Those of ordinary skill in the art will recognize, however, that such measurements may be obtained in any mammal.

The ratio of the T peaks cloud volume to the R peaks cloud volume risk factor can be determined by calculating the ratio of the T peaks cloud volume to the R peaks cloud volume of three dimensional orthogonal ECG measurements of a patient for a selected time period or number of beats reflecting in sinus rhythm of the subject patient. In some examples, the selected number of beats can be from about 30 beats to about 500 beats, or the selected time period can be from about 10 seconds to about 5 minutes.

From an orthogonal ECG, the peaks of R-waves within the interval are first detected manually or automatically via a computer program in 3-D. The peak of R-waves is found by finding the furthest point away from the origin point of the three loops. Peaks of T-waves are detected manually or automatically as well. T-waves were found by maximizing the distance from the origin and also from the R-wave peaks. Magnitudes of R- and T-loop axes were calculated for each beat. The peaks are plotted in 3-D to form an R peaks cloud and T peaks cloud and further analyzed.

As illustrated in Example 3, the R peaks cloud points are used to form a convex hull, and the volume of the R peaks cloud calculated by finding the volume within the convex hull. Volume of T peaks cloud may be calculated in a similar fashion. The volumes of R and T peaks clouds are used to assess variability in depolarization and repolarization respectively. Moreover, the ratio of the R peaks cloud volume to the T peaks cloud volume is calculated to determine risk for occurrence of VT/VF.

Figure 3:
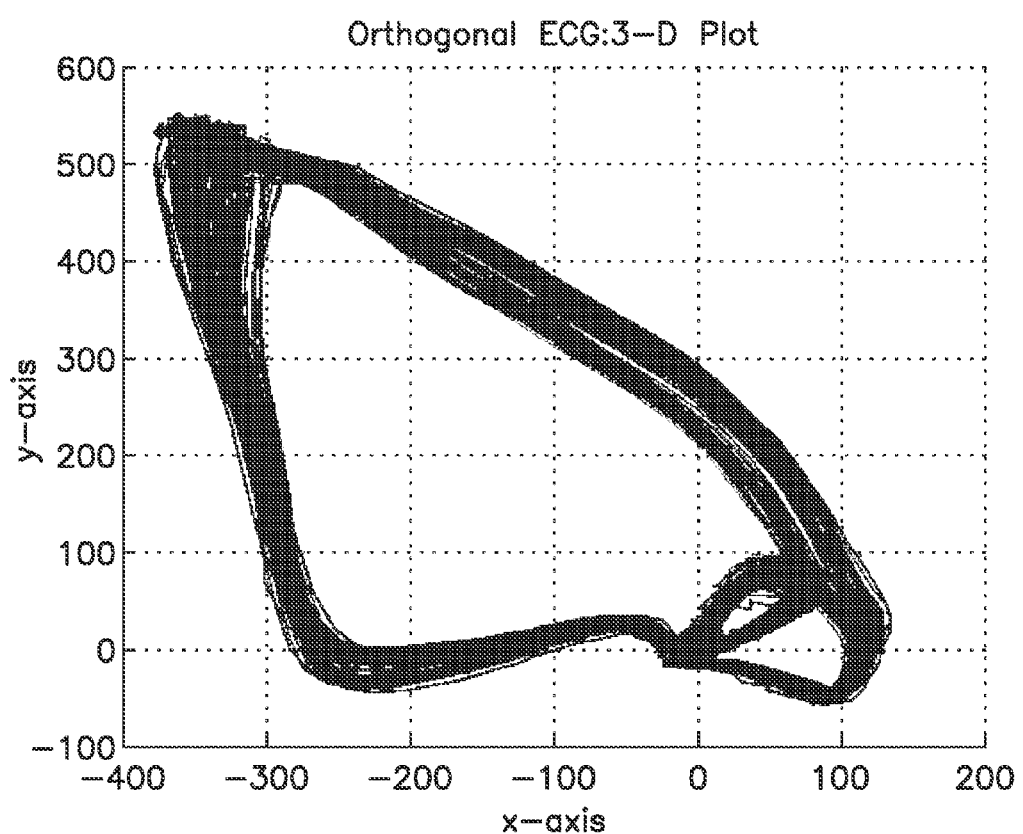
FIG. 3 illustrates QRS- and T-loops plotted in three dimensions.
Figure 4:
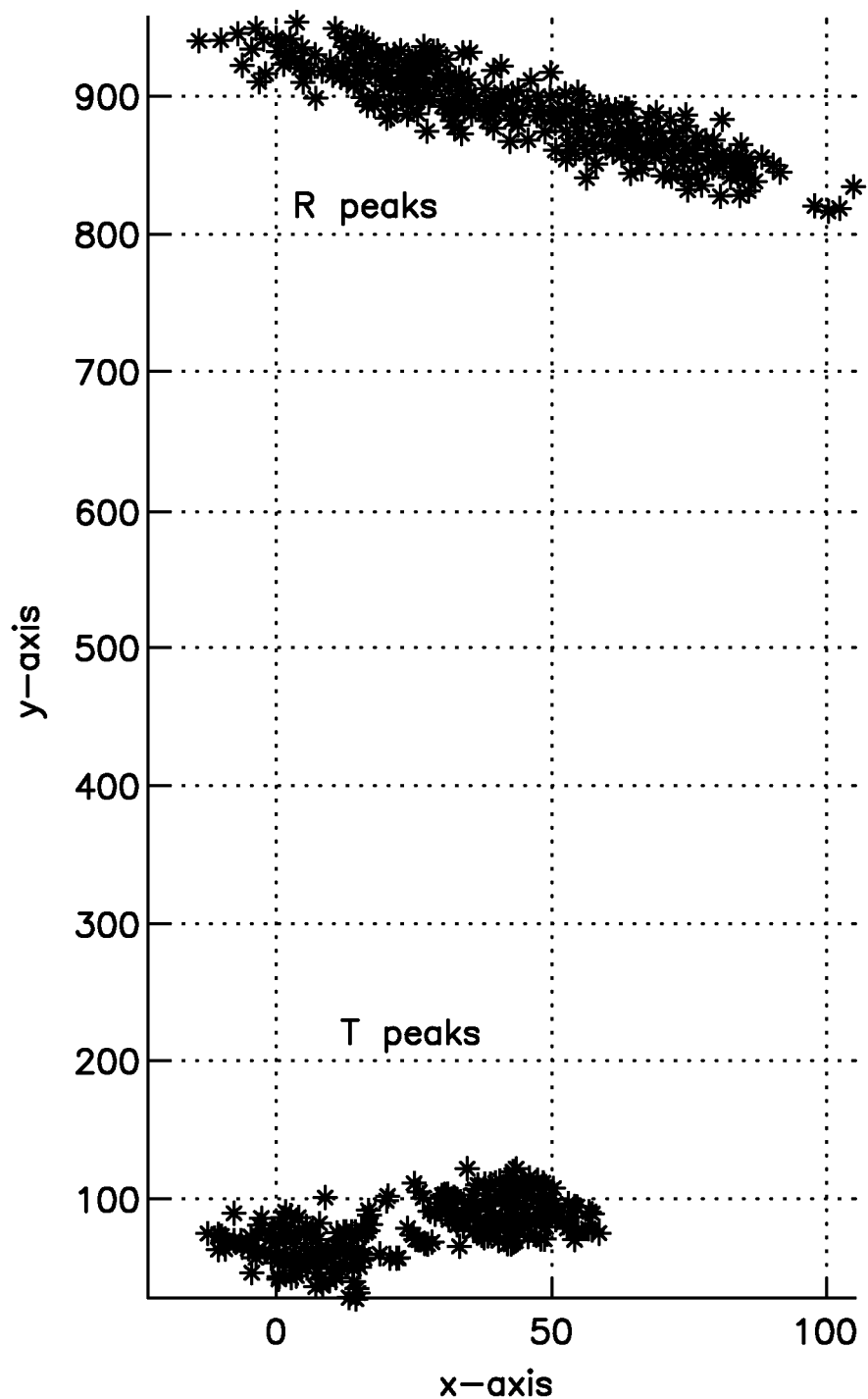
FIG. 4 illustrates an R peak cloud and a T peak cloud.
Figure 5:
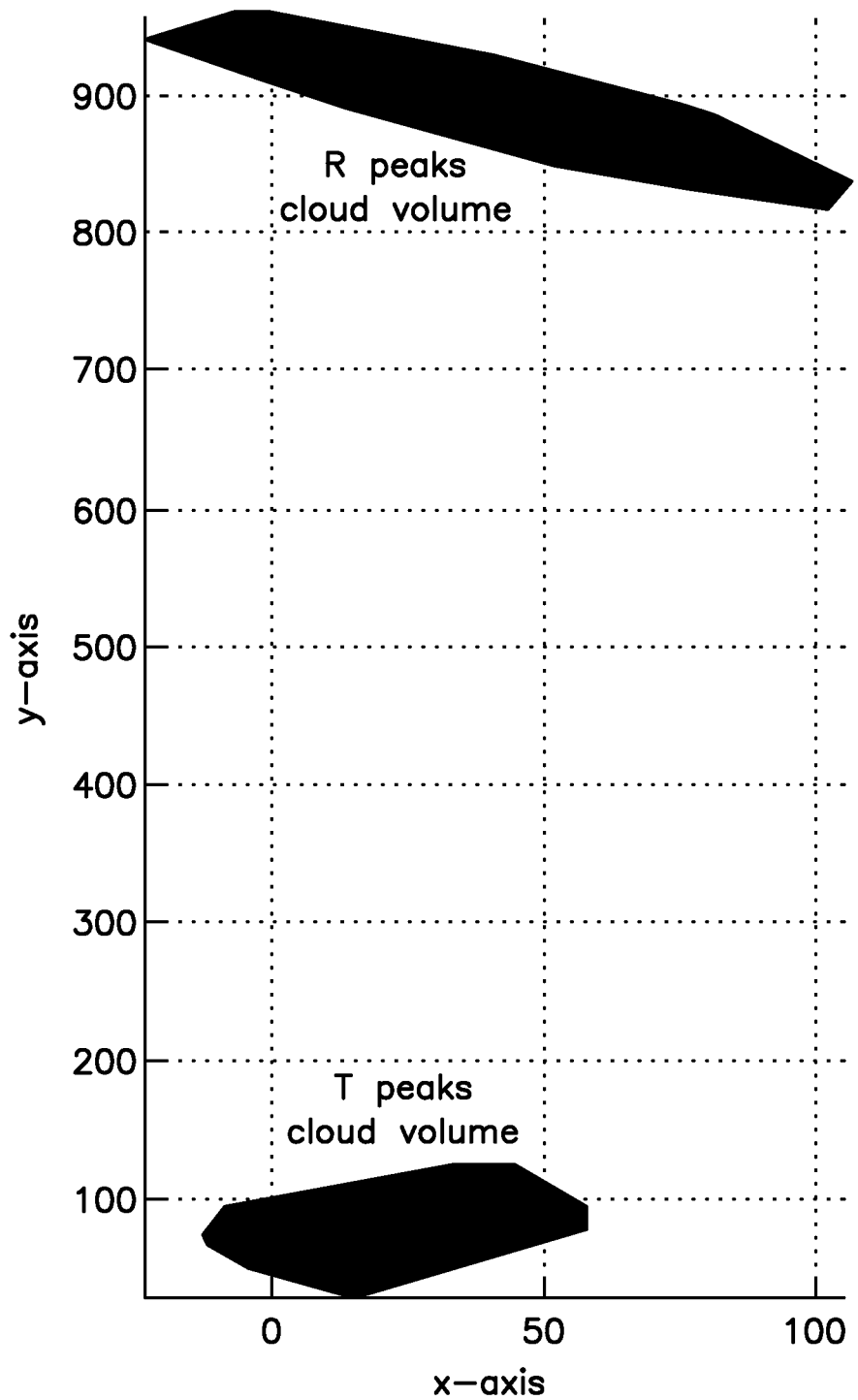
FIG. 5 illustrates an R peak cloud volume and a T peak cloud volume.

Methods of determining a ratio of the T peaks cloud volume to the R peaks cloud volume may include:
  a) Signal pre-processing (baseline wandering and noise elimination).
  b) Plotting QRS—and T-loops in three dimensions (the P-loop can be excluded from analysis), as shown in FIG. 3.
  c) Finding the interloop distance as the shortest distance in space between QRS- and T-loops, located as far as possible in time during RR' interval. Interloop distance connects 2 points: (1) a first point (e.g., a J-point junction between loops), and (2) another corresponding ECG point, located somewhere between the end of T wave and the QRS onset.
  d) Finding the cross-point between QRS- and T-loops by determining an imaginary point in the center of the interloop distance.
  e) Finding the R peak of each QRS-loop by determining the furthest QRS-loop point away from the crosspoint and plotting the R peaks as the R peaks cloud, as illustrated in FIG. 4.
  f) Finding the T peak of each T-loop as the furthest T-loop point away from the crosspoint and plotting the T peaks as the T peaks cloud, as illustrated in FIG. 4.
  g) Calculating the area of the QRS- and T-loops (conveniently may be calculated using a conventional trapezoid rule, with steps starting from the peak of the corresponding loop).
  h) As illustrated in FIG. 5, the R peaks cloud points can be used to form a convex hull, and the volume of the R peaks cloud can be calculated by finding the volume within the convex hull. The volume of the T peaks cloud may be calculated in a similar fashion.

For signal preprocessing as discussed in step (a) above, baseline wandering can be corrected; e.g., by doing a zero order polynomial fit between R-wave peaks and subtracting the difference between the polynomial and the baseline from the data or, in the case of severe baseline wandering, can be corrected with a first order polynomial fit in place of a zero order polynomial. The baseline can be determined as the average of all data points in the interval. This method of baseline correction can be used to minimize distortion of R and T-waves, particularly the ST segment, and can be applied to all data intervals for all three (3) orthogonal leads when surface three (3) lead orthogonal ECG equipment is used.

In general, a cardiac event risk factor of high can be assigned when the ratio of the T peaks cloud volume to the R peaks cloud volume is equal to or greater than about 0.125.

Variability from beat-to-beat in the R/T ratio, especially in the T wave component, is particularly indicative or confirmatory of a high risk of a subsequent cardiac event. The relative volume of the T peaks cloud is significant because patients with ventricular tachyarrhythmia have a relatively large volume of T peaks cloud. This finding is consistent with results of previous studies that showed importance of baseline lability of repolarization. Thus, given similar R peaks cloud volumes, T peaks in patients having a higher risk of a cardiac event, such as VTNF or VA, have a larger volume. Patients with more variability in their T-waves compared to the variability of their R-waves are at higher risk for VT/VF or VA. This volume metric encompasses the overall variability of the segment and represents a complex metric, reflecting the variability in the orientation of the axis in space, and also the magnitude of the axis.

Beat-To-Beat Variability Risk Factor

Risk for occurrence of a subsequent cardiac event can also be determined or predicted from beat-to-beat variability in cardiac vectors visualizable in ECG, especially 3D orthogonal ECG. The selected number of beats used for comparison can be from about 30 beats to about 500 beats. Particular cardiac vectors of interest in this regard comprise SAI QRST, R/T peak volume, spatial QRST angle, T-T' angles, R-R' angles, T-axes amplitudes, R-axes amplitudes, QRS loop areas, and T loop areas. Such variabilities may be considered as indicators of a subsequent cardiac event when evaluated alone, or as confirming or enhancing a risk evaluation made according to other methods of the invention.

For example, as to wide spatial QRS-T angle and increased temporal variability of repolarization indicated thereby, such wide angles are known to predict ventricular arrhythmia. However, direct comparison of the predictive value of spatial QRS-T angle and its variability has not been previously performed. The invention provides a method for assessment of beat-to-beat variability of spatial QRS-T angles which outperforms mean spatial QRS-T angle for VA prediction in patients with structural heart disease.

More particularly, beat-to-beat variability of the spatial QRS-T angle is calculatable as the variance (Var) and root mean square successive difference (rMSSD) between measured values per beat. High QRS-T variability was defined as the highest quartile of either Var or rMSSD values.

Figure 6:
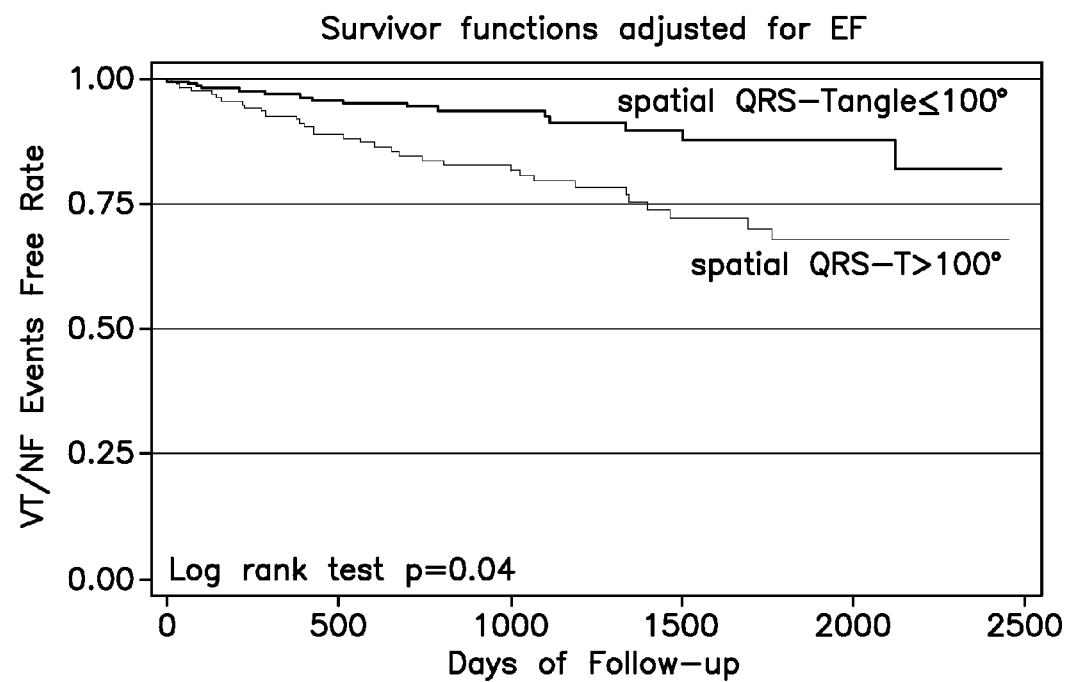
FIG. 6 illustrates variability in spatial QRS-T angles in a class of subjects.
Figure 7:
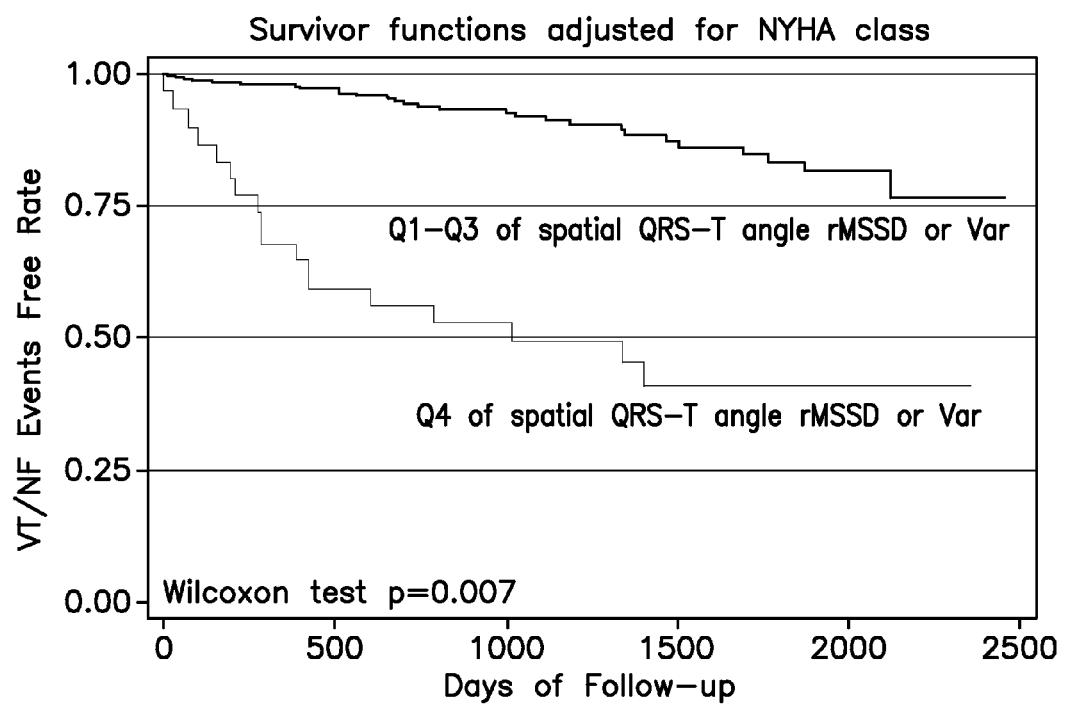
FIG. 7 illustrates variability in spatial QRS-T angles in a class of subjects.

The characteristics of patients in the study of Example 4 with a measured spatial QRS-T angle above and below 90-100° and those with the highest and three lower quartiles of the spatial QRS-T angle variability are shown in FIGS. 6 and 7. Depending on how the data are normalized (e.g., by adjustment for ejection fraction (EF) or NYHA class), VA risk within a 3 to 5 year period following initial evaluation of a patient increased by as much as 25-30%) for those whose spatial QRS-T angle was measured at above 90-100° where the values were adjusted for EF. Further, VA risk over the same period for the same patients increased by as much as 50-60% where the values were adjusted by NYHA class.

As such, spatial QRS-T angle was measured at above 90-100° is a significant indicator of enhanced risk for VA, especially repeat VA, in cardiac patients. In particular, the measure is predictive for a VA event in the 3-5 year period following evaluation at a risk of about 25-60% or greater.

Thus, variance (Var) in the spatial QRST angle of greater than 90 degrees over multiple beats confirms or enhances a determination of high risk for a subsequent cardiac event.

Yet further, a root mean square successive difference (rMSSD) in the measured spatial QRS-T angle>12° between multiple beats confirms or enhances a determination of high risk for a subsequent cardiac event.

In addition, variance (Var) in the measured spatial T-T angle>65° between multiple beats confirms or enhances a determination of high risk for a subsequent cardiac event.

Also, a rMSSD in the measured spatial T-T angle>10° confirms or enhances a determination of high risk for a subsequent cardiac event.

Systems for Use in the Invention

ECG analysis systems for use with the present invention include ECG measuring equipment that obtains three dimensional (3D) orthogonal ECG measurements, and ECG analysis equipment operatively connected to the ECG measuring equipment that receives the three dimensional (3D) orthogonal ECG measurements, executes an ECG analysis program that analyzes the received three dimensional (3D) orthogonal ECG measurements, and provides ECG analysis results in a user readable format.

The ECG analysis system may also include an interactive user interface operatively connected to at least one of the ECG measuring equipment or the ECG analysis equipment, a visual display operatively connected to at least one of the ECG measuring equipment or the ECG analysis equipment, a printer operatively connected to at least one of the ECG measuring equipment or the ECG analysis equipment, or a combination thereof. Operative connections can be any suitable connections that allow data transmission from at least one component of the ECG analysis system to another, and may be wired, wireless, or based on transportable memory media. A transportable memory medium can be any suitable memory medium that connects to a first component of the system and stores data from the first component, and then connects to a second component of the system and transmits the stored data to the second component. An interactive user interface can be any suitable interactive interface that allows a user to input commands or data to a component of the ECG analysis system, including a keyboard, touchpad, or touchscreen. A visual display can be any suitable display device, including a monitor.

Those of ordinary skill in the art will be readily familiar with the types of ECG measuring equipment that can be used to obtain three dimensional (3D) orthogonal ECG measurements, which may include leads and ECG instruments such as surface ECG instruments and intracardiac electrogram instruments. One example of ECG measuring equipment that can be used in practicing the present invention includes Frank or modified Frank orthogonal XYZ leads used with a conventional surface ECG instrument (leads and other ECG equipment are available, for example, through Norav Medical Ltd, Thornhill, ON, Canada). Preferably, the ECG measuring equipment may perform an ECG at a 1000 sampling/sec frequency, which provides clarity of waveform quality.

The ECG measuring equipment can obtain ECG data and transmit data to the ECG analysis equipment. The ECG analysis equipment executes an ECG analysis program and provides ECG analysis results in a user readable format, such as by displaying the ECG analysis results on a visual display, by printing the ECG analysis results, or a combination thereof. The ECG analysis equipment includes a computing device that may be a standard desktop, laptop, palmtop, server-based, and/or any suitable computing device or architecture capable of executing the ECG analysis program. In this regard, the computing device is suitably configured to perform any number of functions and operations associated with the management, processing, retrieval, and/or delivery of data, and it may be configured to run on any suitable operating system such as Unix, Linux, the Apple Macintosh OS, or any variant of Microsoft Windows. Furthermore, the computing device may employ one or more processors, such as one or more microprocessors, which may be from the Pentium family of processors by Intel or the processor devices commercially available from Advanced Micro Devices, IBM, Sun Microsystems, or Motorola.

In executing the ECG analysis program, the one or more processors can communicate with system memory (e.g., a suitable amount of random access memory), and an appropriate amount of storage or "permanent" memory. The permanent memory may include one or more hard disks, floppy disks, CD-ROM, DVD-ROM, magnetic tape, removable media, solid state memory devices, or combinations thereof. In accordance with known techniques, operating system programs and the application programs associated with the ECG analysis system can reside in the permanent memory and portions thereof may be loaded into the system memory during operation.

When implemented in software, various elements of the present invention are essentially the code segments, computer program elements, or software modules that perform the various tasks, including analysis or calculation steps as described herein with respect to the ECG analysis methods. The program or code segments can be stored in a processor-readable medium or transmitted by a computer data signal embodied in a carrier wave over any suitable transmission medium or communication path. The "processor-readable medium" or "machine-readable medium" may include any medium that can store or transfer information. Examples of the processor-readable medium include an electronic circuit, a semiconductor memory device, a ROM, a flash memory, an erasable ROM (EROM), a floppy diskette, a CD-ROM, an optical disk, a hard disk, a fiber optic medium, a radio frequency (RF) link, or the like. The computer data signal may include any signal that can propagate over a transmission medium such as electronic network channels, optical fibers, air, electromagnetic paths, or RF links. The code segments may be downloaded via computer networks such as the Internet, an intranet, a LAN, or the like.

The invention having been fully described, its practice is illustrated by the Examples bellow. The Examples represent use of the invention but do not limit its scope, which is defined solely by the appended claims.

Example 1

Study on SAI QRST

The study protocol was approved by the Johns Hopkins University IRB, and all patients gave written informed consent before entering the study.

Study Population

PROSE-ICD (NCT00733590) was conducted as a prospective observational multicenter cohort study of primary prevention ICD patients with both ischemic and non-ischemic cardiomyopathy. Reported study participants were recruited at the Johns Hopkins Hospital. Patients were eligible for the study if the left ventricular (LV) ejection fraction (EF) was less than or equal to 35%, myocardial infarction was at least 4 weeks old, or non-ischemic LV dysfunction was present for at least 9 months. Patients were excluded if the ICD was indicated for secondary prevention of SCD, if patient had a permanent pacemaker or a Class I indication for pacing, if the patient had NYHA (New York Heart Association) class IV, or if the patient was pregnant. Electrophysiologic testing to assess inducibility of VT was performed in 373 patients (73%) at the time of ICD implantation. Left ventricular diastolic diameter (LVDD) was assessed by two-dimensional echocardiography in 225 patients (44.3%). Single-chamber ICD was implanted in 263 patients (52%), dual-chamber ICD in 92 patients (18%), and cardiac resynchronization therapy defibrillator (CRT-D) in 153 patients (30%).

Surface ECG Recording

Digital orthogonal ECG was recorded before primary ICD implantation during 5 minutes at rest in study participants, using the modified Frank orthogonal XYZ leads by PC ECG machine (Norav Medical Ltd, Thornhill, ON, Canada), with a 1000 Hz sampling frequency, filtered at 35 and 60 Hz.

QRST Integral Measurement

All ECGs were analyzed by customized software in a robust automated fashion. Noise and ventricular premature and ventricular-paced beats were excluded from analysis, but ECG recordings during atrial fibrillation were analyzed. Images of areas under the QRST curve were reviewed to ensure appropriate ECG wave detection. Absolute QRST integral was measured as the arithmetic sum of areas under the QRST curve (absolute area under the QRST curve above baseline was added to the area below baseline, FIGS. 1 and 2), averaged during a 5-min epoch. The sum magnitude of 3 orthogonal leads absolute QRST integral (SAI QRST) was calculated.

Endpoints

Appropriate ICD therapies (either shock or antitachycardia pacing (ATP)) for VTs served as the primary endpoint for analysis. Programming of the ICD was based on the attending electrophysiologist's clinical evaluation. The ICD device was interrogated during follow-up visits every 6 months. All ICD interrogation data were reviewed by an independent endpoints adjudication committee, blinded to the results of SAI QRST analysis. ICD therapies for monomorphic ventricular tachycardia (MMVT), polymorphic ventricular tachycardia (PVT), or ventricular fibrillation (VF) was classified as appropriate. MMVT was defined as a sustained VT with stable cycle length and electrogram morphology. PVT was defined as a sustained VT with unstable cycle length and electrogram morphology and average cycle length>200 ms. VF was defined as sustained ventricular tachyarrhythmia with unstable cycle length and electrogram morphology and average cycle length<200 ms. Sustained appropriately treated VTNF events were categorized as MMVT group and PVTNF group.

Statistical Analysis

The first 128 consecutive participants of the study were included in the derivation cohort. The validation cohort included the remaining 380 study participants who were followed prospectively at least 6 months.

There were no statistically significant differences between baseline characteristics of derivation and validation cohort patients. Rate of VTNF events did not differ as well (15 patients (11.1%) in derivation cohort vs. 43 patients (11.3%) in validation cohort experienced VTNF (P=0.901 V). A few differences in patient management were observed: derivation cohort patients were more frequently on beta-blockers and statins, with slightly higher revascularization procedures rate.

Derivation Dataset Analysis.

Cut-off points of SAI QRST were determined in the preliminary analysis of 128 study patients 15 had sustained VT/VF events during 13±10 months of follow-up. In this derivation set the lowest SAI QRST quartile was <69 mV*ms, and the highest quartile was >145 mV*ms. Preliminary survival analysis of the derivation set showed that the lowest quartile of the SAI QRST predicted VT/VF (log rank test P<0.0001) with 100% sensitivity, 78% specificity, 37% positive predictive value, and 100% negative predictive value (see, e.g., FIG. 9).

Validation Dataset Analysis.

Figure 9:
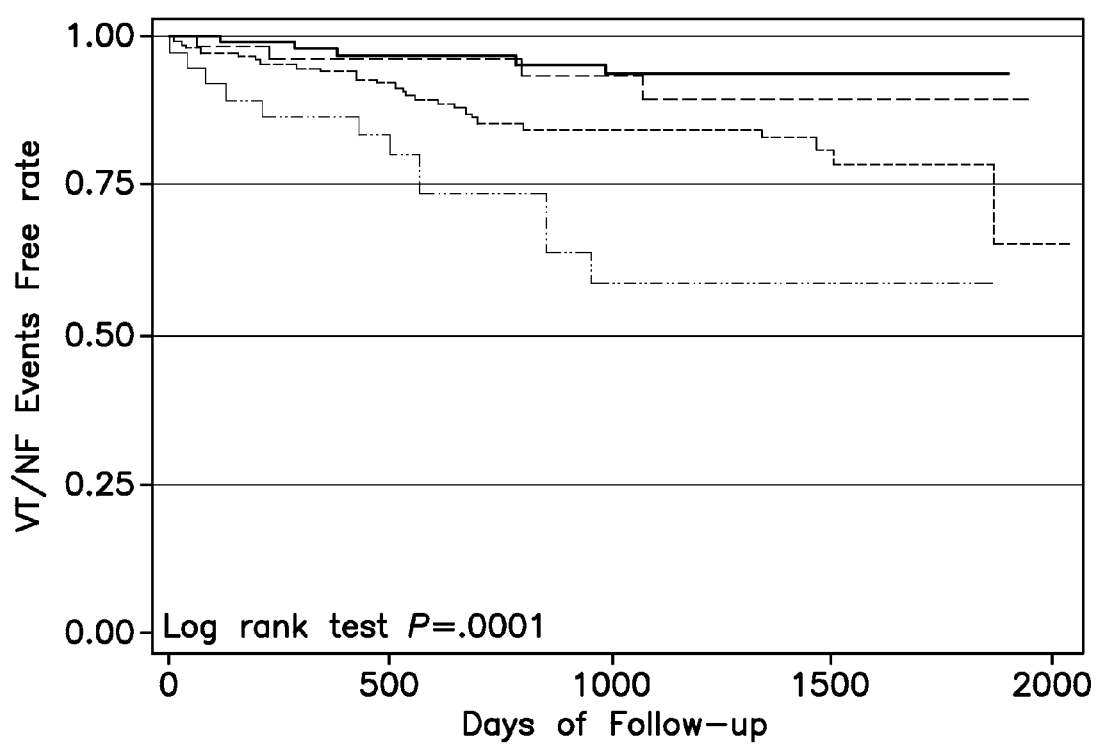
FIG. 9 contains Kaplan-Meier curves for freedom from VA events in patients with low, intermediate and high SAI QRST, adjusted by QRS width.

Validation cohort participants were categorized according to their baseline SAT QRST value, with SAI QRST<69 mV*ms labeled low, SAI QRST 70-145 mV*ms labeled intermediate, and SAI QRST>145 mV*ms labeled high (FIG. 8). Linear regression analysis was used to study what physiologic parameters correlate with the SAI QRST. One-way ANOVA was used to compare among 3 groups of SAI QRST, with Bonferroni correction for multiple comparisons. Unadjusted and adjusted Kaplan-Meier survival curves were constructed for subjects with low, intermediate, or high SAT QRST (FIG. 9). The log-rank (Mantel-Cox) statistic was computed to test the equality of survival distributions. Univariate and multivariate Cox proportional hazards regression analysis was performed. An interaction between SAI QRST and bundle branch block (BBB) status, as well as between SAI QRST and LVDD was tested in the Cox model. The receiver operating characteristic (ROC) curves, sensitivity, specificity, and predictive values of SAI QRST for freedom from VT/VF were calculated. STATA 10 software (StataCorp LP, College Station, Tex.) was used for calculations.

Results

Ventricular Tachyarrhythmias During Follow-Up

During a mean follow-up of 18.0±16.5 months, 43 (11.43% or 7.5% per person-year of follow-up) of the 380 validation cohort patients experienced sustained VTs and received appropriate ICD therapies. MMVT with an average cycle length (CL) of 2934±38 ms was present in 31 patients (72%). PVT/VF with an average CL 214±18 ms was documented in 12 patients (3.2% or 2.1% per person-year of follow-up"). There were significantly fewer patients on beta-blockers among those patients receiving subsequent appropriate ICD therapies (Table 2). There was no difference in MMVT rate between ICD and CRT-D patients. However, a trend toward less frequent PVT/VF events in CRT-D recipients was noticed. PVT/VF was observed in 7 patients with single-chamber ICD (3.7%), in 4 patients with dual-chamber ICD (5.2%), but only 1 CRT-D patient (0.9%)[P=0.210]. SAI QRST was significantly lower in patients with sustained VTs during follow-up. All VT/VF events but one were observed among patients with low or intermediate SAI QRST (i.e., ≥145 mV*ms).

In the univariate Cox proportional hazards analysis, patients with low SAI QRST double the risk of VT/VF (hazard ratio (HR) 2.25; 95% confidence interval (CI): 1.35-3.77, p=0.002). Low SAI QRST predicts MMVT (HR 2.34; 95% CI 1.25-4.37; p=0.008), rather than PVT/VF (HR 2.08; 95% CI 0.84-5.12; p=0.114). Importantly, risk of VT/VF in patients with high SAI QRST was 10-fold less (HR 0.11; 95% CI: 0.01-0.80, p=0.030). Patients with high SAI QRST were completely free from MMVT. However, prediction of freedom from PVT/VF with high SAI QRST did not reach statistical significance (HR 0.36; 95% CI 0.046-2.80; p=0.329).

Several parameters were statistically significantly correlated with the SAI QRST: age (r=0.097, p=0.029), LVDD (r=0.149, p=0.018), EF (r=−0.128, p=0.004), heart rate (r=−0.105, p=0.018), duration of the QT interval (r=0.233, p<0.0001)[FIG. 5B1D], beat-to-beat QT variability index (r=−0.176, p<0.0001), and QRS width (r=0.650, p<0.0001). SAI QRST was significantly higher in patients with either left or right complete BBB (178.46±92.06 vs. 94.01±49.65, p<0.00001), and it was diminished in patients with ischemic cardiomyopathy (102.28±61.16 vs. 128.35±80.89, p=0.0001), in patients on statins (86.60±41.14 vs. 107.79±66.88, p=0.003), and in patients on ACE-I (85.06±56.06 vs. 111.82±68.95, p=0.004).

Multivariate Survival Analysis

Because QRS width and QT duration along with proportion of females and ischemic cardiomyopathy patients with history of revascularization procedures were different among SAI QRST groups, the multivariate model of VT/VF prediction was adjusted by above-named parameters. Neither gender nor etiology of cardiomyopathy was significant predictors of VT/VF events. Among other parameters, only LVDD was significant in univariate Cox regression. Neither QT nor QRS duration predicted VT/VF events. Various cut-offs of QRS duration (>120 ms, >130 ms, >150 ms) did not improve predictive value of QRS duration.

No significant interaction was found between SAI QRST and presence of BBB, between SAI QRST and LVDD. In the multivariate Cox regression analysis for VT/VF events, high SAI QRST remained a significant predictor of freedom from VT/VF after adjustment for QT, LVDD, QRS width or BBB, gender, type of cardiomyopathy, and history of revascularization procedures.

The ROC curve measuring the accuracy of the SAI QRST for freedom from VT/VF showed an AUC of 0.682 (95% CI: 0.602-0.761). SAI QRST<145 mV*ms demonstrated 98% sensitivity, 33% specificity, 14% positive predictive value, and 99% negative predictive value for prediction of VT/VF during 1.5 years of follow-up.

SAI QRST and QRS Width

No significant interaction was found between SAI QRST and presence of BBB in the multivariate Cox regression model, which means that SAI QRST predicts VT/NF in patients with and without BBB. However, SAI QRST was significantly larger in patients with either left or right complete BBB (178.46±92.06 vs. 94.01±49.65, p<0.00001). Therefore we suggest that the best cut-off value of SAI QRST should be different for patients with wide vs. narrow QRS. For the purpose of this analysis we combined derivation and validation cohorts and categorized all 508 study patients as narrow QRS subgroup (QRS≤120 ms, N=272, [53.5%]) and wide QRS subgroup (QRS>120 ms, N=236[46.5%]). To define the best SAI QRST cutoff value, ROC curves were constructed separately in patients with narrow and wide QRS. In patients with narrow QRS≤120 ms the SAI QRST 69.4 mV*ms provided 58% sensitivity and 56% specificity. In patients with wide QRS>120 ms the SAI QRST 133.7 mV*ms provided 55% o sensitivity and 92% specificity.

In the univariate analysis QRS width alone did not predict VA. However, both SAI QRST and QRS width were significant predictors of VA events in a multivariate Cox regression model that included SAI QRST and QRS width as continuous variables, type of cardiomyopathy and use of beta-blockers. In the bivariate Cox regression model every 1 ms of incremental QRS widening with simultaneous 1 mV*ms SAI QRST decrease raised risk of VT/NF by 2% (HR 1.02; 95% CI 1.01-1.03, p=0.005). Thus, QRS width is associated with ventricular tachyarrhythmia only if accompanied by low SAI QRST. Patients with subsequent VT/NF were notably different in this regard, whereas in all study patients every 1 ms of incremental QRS widening was accompanied by simultaneous 3 mV*ms SAI QRST increase. Notably, SAI QRST predicted VT/VF events in patients with any QRS width. Surprisingly, the predictive accuracy of SAI QRST in patients with wide QRS>120 ms was at least as good as in patients with narrow QRS≤120 ms.

SAI QRST and Left Ventricular Size

These results revealed significant correlation between SAT QRST and left LV diastolic diameter (LVDD). Of note, PROSE-ICD study patients at baseline had remarkably impaired systolic function, LV dilatation, and frequently a large area of myocardial scar. Several previous other studies, focused on healthier population of hypertensive patients, showed that Cornell voltage-duration product (RaVL+SV3 [+6 mm in women]*QRS duration) is associated with the risk of SCD. Interestingly, in contrast to these findings, a large instead of a small Cornell voltage-duration product was associated with the risk of SCA.

Example 2

Low Frequency (10-50 Hz band) SAI QRST

SAI QRST Analysis of Systolic HF Patient Population in MADIT II Study

The MADIT II study is a known study conducted by Boston Scientific. Design and outcomes of MADIT II study are well known and results have been extensively published during the last decade (see, e.g., Moss, *Eur Heart J*, 24 (1): 16-18 (2003)). Briefly, 1,232 patients with documented previous myocardial infarction (MI) and EF≤30% were randomized to receive a prophylactic ICD or conventional medical therapy in a 3:2 ratio and were followed over a mean period of 20 months. Patients were excluded if they were in NYHA functional class IV at enrollment; had undergone coronary revascularization within the preceding 3 months; had MI within the past month; had advanced cerebrovascular disease; had blood urea nitrogen (BUN)>70 mg/dl or creatinine>3.0 mg/dl.

Blinded analysis of the baseline ECGs and survival analysis was performed to provide population standardized risk factors for use in the invention. For example, proposed predictors of VA, including SAI QRST, QRST integral, and low frequency (10 Hz to 50 Hz band) SAI QRST can be measured as continuous variables and then can be dichotomized or separated based on quartiles, as reflected in FIGS. 1 and 2. Variation of variables of interest can be defined, and Log transformation (or other transformation, if required, depending on the particular case) performed for any variable that displays non-normal distribution, with subsequent verification of an achieved normal distribution. Simple and multiple linear regression models may be explored to determine factors that may play the role of predictors of our tested marker of interest, presented as a continuous variable. For such linear regression models, the tested marker can be an outcome variable.

Continuous variables can be compared using the independent samples t test if normally distributed and the Wilcoxon rank sum test if skewed. The Pearson chi-square test can be used to compare categorical variables. A p-value of <0.05 can be considered significant. Kaplan-Meier survival analysis can be used to compute mean and median survival time, with standard error and 95% confidence interval. The log-rank (Mantel-Cox) statistic can be computed to test the equality of survival distributions. A Cox proportional hazards analysis can be performed separately for each variable of interest. Multivariate Cox regression models can include tested SAI QRST markers along with known clinical and demographic predictors of outcomes. A non-parametric proportional hazards model can also be used to explore possible transformations of the independent variables in the model, including generalized gamma distribution family and generalized regression models. ROC analysis can be performed and AUC can be calculated for every tested marker of risk. Multiple ROC AUCs can be compared.

The Multicenter Ultrasound Stenting in Coronaries Study (MUSIC Study; see, e.g., de Jaegere, et al., *Eur Heart J.*, 19(8):1214-23 (1998)) is also a source of population standardized data for risk factor development for use in the invention. Such factors are provided through analysis of baseline SAI QRST along with low frequency (10-50 Hz band) SAI QRST in population of patients with HFpEF, in comparison to patients with systolic HF in the MUSIC study, blinded analysis of baseline ECGs and survival analysis was performed.

For example, in a group of 651 patients with HF and sinus rhythm enrolled in the MUSIC study, there are 294 patients with HFpEF, aged 18-89 years (mean 66±12 years). The majority of patients were in NYHA heart failure class II (86%). Ischemic cardiomyopathy accounted for 45% of patients. LVEF varied from 36-70% with a mean of 49±11%. During a median 44-month follow up there were 43 deaths, including 36 cardiac deaths and 7 noncardiac deaths, in 294 patients. Cardiac death included 15 sudden and 21 non-sudden deaths.

Statistical power may be insufficient in the subgroup of patients with HFpEF to detect differences in survival time if expected hazard ratio would be below 5, which may be the case for QRST integral and low frequency SAI QRST. However, the preliminary analysis of SAI QRST conducted in Example 1 demonstrated hazard ratio above 5, in the range of from about 7 to about 12, which may permit survival analysis in HFpEF population.

To provide further population standardized data for risk factor development for use in the invention through analysis of the associations between SAI QRST and MRI-assessed characteristics of geometry, hypertrophy, dilatation of the heart, and scar characteristics in patients with structural heart disease and implanted primary prevention ICD, the data from the study of Example 1 can be analyzed by simple and multiple linear regression models to determine factors that may play the role of predictors of SAI QRST, presented as a continuous variable. MRI data of subset of PROSE_ICD study patients (N=200) can be analyzed. Contrast-enhanced MRI (ceMRI) can be used to quantify myocardial infarct heterogeneity, to measure LV function, volumes, mass, and infarct size.

Example 3

Study on Beat-to-Beat Variability of 3D ECG Cardiac Vectors

The data of 81 participants of the PROSE-ICD study (NCT00733590), discussed in Example 1 above, were analyzed. This study primarily altered the analysis of temporal variability by moving analysis from 2-dimensions to 3-dimensions. Whereas the vectorcardiography (VCG) method was proposed about a century ago, everyday use of VCG in clinical practice is limited. However, analysis in 3D can have many advantages over analysis in 2D, primarily in visualization, PVC detection, and wave detection. While peak detection is straightforward in ECGs, it can be difficult to robustly detect the beginning and end of waves, especially the T-wave. However, in 3D, it is clearer when the T-wave is leaving and when it has reached the origin point. In addition, this 3-D volume analysis can be calculated for almost all orthogonal ECGs. See, e.g., FIG. 3 for an image of waves represented as loops in 3D output from an orthogonal ECG.

Preparation for Epoch Analysis

For data analysis, 30 beat intervals of data in sinus rhythm were selected from each patient. Baseline wandering was subsequently corrected by doing a zero order polynomial fit between R-wave peaks and subtracting the difference between the polynomial and the baseline from the data. Severe baseline wandering was corrected with a first order polynomial fit in place of a zero order polynomial. The baseline was determined as the average of all data points in the interval. This method of baseline correction was used to minimize distortion of R and T-waves, particularly the ST segment. The method was applied to all data intervals for all 3 orthogonal leads. Severe noise present was filtered with a low-pass filter, and PVC beats were manually excluded prior to analysis.

Variability Analysis

Variability of both depolarization and repolarization were measured using a complex volume metric. From an orthogonal ECG, the peaks of R-waves within the interval were first detected automatically in 3-D using custom designed software written in MATLAB (MathWorks, Inc., Natick, Mass.). The peak of R-waves was found by finding the furthest point away from the origin point of the three loops. Peaks of T-waves were detected automatically by the software as well. T-waves were found by maximizing the distance from the origin and also from the R-wave peaks. Magnitudes of R- and T-loop axes were calculated for each beat. Outputs were saved and individually reviewed to ensure accuracy and quality of detection using this new method of detection from 3-D coordinates. These peaks were plotted in 3-D to form an R peaks cloud and a T peaks cloud (see, e.g., FIGS. 4 and 5) and further analyzed.

The R peaks cloud points were used to form a convex hull, the convex shape with the smallest volume necessary to encompass all the R-wave peak points. The volume of the R peaks cloud was then calculated by finding the volume within the convex hull. Volume of T peaks cloud was calculated in a similar fashion. The volumes of R and T peaks clouds were used to assess variability in depolarization and repolarization respectively. In addition, the ratio of the R peaks cloud volume to the T peaks cloud volume was calculated.

Endpoints

Patients who sustained VT/VF were treated with appropriate ICD therapies, either with ICD shock or with anti-tachycardia pacing, which was the endpoint for this analysis. Follow-up visits occurred every 6 months during which time the ICD device was interrogated. The interrogation data was adjudicated by a committee of 3 independent electrophysiologists. The committee classified the appropriate ICD therapies into VF, polymorphic tachycardia, and monomorphic ventricular tachycardia.

Statistical Analysis

All statistics were computed using STATA 10 (StataCorp LP, College Station, Tex.). Normally distributed continuous variables were compared using Student's t-Test and skewed continuous variables were compared using the Wilcoxon Rank-Sum Test. For this preliminary study of 81 patients, Wilcoxon Rank-Sum Test was applied to R peaks cloud volumes and T peaks cloud volumes. Student's t-test was done on the R/T peaks cloud ratio and also T/R peaks cloud ratio. Linear regression analysis was performed to see if any clinical characteristics correlated with volume findings.

Results

Half of the study population's patients had ischemic cardiomyopathy. All patients received beta-blockers. Right bundle branch block at baseline was documented in 2 patients. History of atrial fibrillation was found in 14 patients (17%) at baseline. However, all baseline analyzed ECG were in sinus rhythm only. During a mean follow up time of 13±10 months, 9 out of the 81 patients (11%) experienced sustained VT/VF with appropriate ICD therapies.

R Peaks Cloud Volume and T Peaks Cloud Volume Analysis

R peaks cloud volume was not found to be significantly different between patients who sustained VT/VF and those who did not. In linear regression analysis, R peaks cloud volume was found to significantly correlate with the mean magnitudes of R-wave axis ($p=0.008$) and with the variance of R-wave axis magnitude ($p<0.0001$). R peaks cloud volume was not found to correlate with heart rate ($p=0.11$).

T peaks cloud volume was also not found to be significantly different between patients with sustained VTNF and those who did not ($p=0.25$). In linear regression analysis, T peaks cloud volume significantly correlated with the variance of T-wave axis magnitude ($p=0.001$), and did not correlate with mean magnitude of T-wave axis ($p=0.54$) or heart rate ($p=0.15$).

R/T peaks cloud volumes ratio was significantly lower in patients that sustained VT/VF than those that did not. R/T peaks cloud ratio was not found to significantly correlate with age ($p=0.508$), LVEF ($p=01283$), or other clinical parameters such as BMI, blood pressure, or blood sugar.

Accordingly, it was determined that patients with ventricular tachyarrhythmia have a relatively large volume of T peaks cloud. This finding is consistent with results of previous studies that showed importance of baseline lability of repolarization. Notably, direct comparison of R peaks cloud volumes and T peaks cloud volumes did not show difference between patients with and without VTNF. However, the ratio of R peaks cloud volume to T peaks cloud volume was significantly lower in patients who sustained VTNF during followup.

This demonstrates that, given similar R peaks cloud volumes, T peaks in patients having a higher risk of VT/VF had a larger volume. This can be interpreted to signify that patients with more variability in their T-waves compared to the variability of their R-waves are at higher risk for VT/VF. This volume metric encompasses the overall variability of the segment analyzed and represents a complex metric, reflecting the variability in the orientation of the axis in space, and also the magnitude of the axis. Interestingly, R peaks cloud volume strongly correlated with the mean axis amplitude of all R-wave axes, but the same did not hold true for the T-wave. Thus, this shows that the R-wave variability is affected by the size of the R-wave loop much more so than for the T-wave, which follows logically as bigger loops can produce larger variability.

Example 4

Beat-To-Beat Variability of Spatial QRS-T Angle

Further, analysis of the data from the study patients referenced in Example 3 indicates that beat-to-beat variability of spatial QRS-T angle outperforms mean spatial QRS-T angle for VA prediction in patients with structural heart disease. Beat-to-beat variability of the spatial QRS-T angle was calculated as the variance (Var) and root mean square successive difference (rMSSD). High QRS-T variability was defined as the highest quartile of either one.

Depending on whether the data are normalized (e.g., by adjustment for ejection fraction (EF) or NYHA class), VA risk within a 3 to 5 year period following initial evaluation of a patient increased by as much as 25-30%) for those whose spatial QRS-T angle was measured at above 100° where the values were adjusted for EF. Further, VA risk over the same period for the same patients increased by as much as 50-60% where the values were adjusted by NYHA class. See, FIGS. 6 and 7.

As such, spatial QRS-T angle was measured at above 100° is a significant indicator of enhanced risk for VA, especially repeat VA, in cardiac patients (e.g., those in the study, whose prior history included left ventricular (LV) ejection fraction (EF) was less than or equal to 35%, myocardial infarction that was at least 4 weeks old, or non-ischemic LV dysfunction present for at least 9 months).

From the foregoing, it will be appreciated that although specific examples have been described herein for purposes of illustration, various modifications may be made without deviating from the spirit or scope of this disclosure. It is therefore intended that the foregoing detailed description be regarded as illustrative rather than limiting, and that it be understood that it is the following claims, including all equivalents, that are intended to particularly point out and distinctly claim the claimed subject matter.

What is claimed is:

1. A method for analyzing ECG measurements obtained from a patient to determine a patient risk factor corresponding to a level of risk of the patient experiencing a subsequent cardiac event, the method comprising the steps of:
   (a) obtaining orthogonal ECG measurements of a patient with 3D ECG measuring equipment; and
   (b) providing the obtained ECG measurements to ECG analysis equipment that receives the ECG measurements, performs an ECG analysis, and provides ECG analysis results in a user readable format;
   wherein the ECG analysis includes determining at least one cardiac event risk factor having a value, the at least one cardiac event risk factor being determinable from one or more cardiac vector values selected from: sum magnitude of absolute QRST integral (SAI QRST), R/T peaks volume, spatial QRST angle, T-T' angles, R-R' angles, T-axes amplitudes, R-axes amplitudes, QRS loops areas, T loops areas, beat-to-beat variability in sum magnitude of absolute QRST integral (SAI QRST), beat-to-beat variability in R/T peaks volume, beat-to-beat variability in spatial QRST angle, beat-to-beat variability in T-T' angles, beat-to-beat variability in R-R' angles, beat-to-beat variability in T-axes amplitudes, beat-to-beat variability in R-axes amplitudes, beat-to-beat variability in QRS loops areas, and beat-to-beat variability in T loops areas,
   wherein the ECG measurement equipment includes a surface ECG instrument and the ECG measurements are expressed as three lead orthogonal ECG data or the ECG measurement equipment includes an intracardiac electrogram instrument, and
   wherein the cardiac event risk factor is a SAI QRST that is determined by plotting a QRST curve for each lead of the expressed three lead orthogonal ECG data or for the ECG measurements,
   and calculated via the total sum of the absolute areas under the QRST curve for each of the three leads or the intracardiac electrogram instrument.

2. The method of claim 1, wherein the ECG measurements are obtained from a patient at rest during a rest time period that is from 2 minutes to 10 minutes.

3. The method of claim 1, further comprising determining a ratio of a T peaks cloud volume to a R peaks cloud volume determined by calculating the ratio of the T peaks cloud volume to the R peaks cloud volume of three dimensional orthogonal ECG measurements of a patient for a selected time period or number of beats.

4. The method of claim 3, wherein the selected time period or number of beats is from 30 beats to 500 beats.

5. The method of claim 4, wherein variability of the SAI QRST values from beat to beat is indicative of a high risk of a subsequent cardiac event.

6. The method of claim 1, further comprising a step of:
   (c) assigning a cardiac event risk factor of low, intermediate, or high based upon the value of the at least one cardiac event risk factor.

7. The method of claim 6, wherein the cardiac event risk factor is a SAI QRST, and the cardiac event risk factor is low when the SAI QRST is equal to or greater than 145 mV*ms.

8. The method of claim 6, wherein the cardiac event risk factor is a SAI QRST, and the cardiac event risk factor is intermediate when the SAI QRST is from 70 mV*ms to 145 mV*ms.

9. The method of claim 6, wherein the cardiac event risk factor is a SAI QRST, and the cardiac event risk factor is high when the SAI QRST is less than 69 mV*ms.

10. The method of claim 6, wherein the SAI QRST evaluation is utilized to screen patients with structural heart disease for implantation of an ICD (intracardiac device).

11. The method of claim 1, wherein the cardiac event risk factor that is determined is the ratio of the T peaks cloud volume to the R peaks cloud volume, wherein a R/T ratio of 0.125 or lesser is indicative of a high risk of a subsequent cardiac event.

12. The method of claim 1, wherein beat-to-beat variability in one or more of the cardiac vectors is indicative of a high risk of a subsequent cardiac event.

13. The method of claim 12, wherein the variability is detected as a variance (Var) in the spatial QRST angle of greater than 90 degrees over multiple beats, and such detection confirms or enhances a determination of high risk for a subsequent cardiac event.

14. The method of claim 12, wherein the variability is detected as a root mean square successive difference (rMSSD) in the measured spatial QRS-T angle>12° between multiple beats, and such detection confirms or enhances a determination of high risk for a subsequent cardiac event.

15. The method of claim 12, wherein the variability is detected as Var in the measured spatial T-T' angle>65° between multiple beats, and such detection confirms or enhances a determination of high risk for a subsequent cardiac event.

16. The method of claim 12, wherein the variability is detected as a rMSSD in the measured spatial T-T' angle>10°, and such detection confirms or enhances a determination of high risk for a subsequent cardiac event.

17. An ECG analysis system for analyzing ECG measurements obtained from a patient to determine a patient risk factor corresponding to a level of risk of the patient experiencing a subsequent cardiac event, the ECG analysis system comprising:
   (a) 3D ECG measuring equipment that obtains orthogonal ECG measurements; and
   (b) ECG analysis equipment operatively connected to the ECG measuring equipment that receives the ECG measurements, performs an ECG analysis, and provides ECG analysis results in a user readable format;

wherein the ECG analysis includes determining at least one cardiac event risk factor having a value, the at least one cardiac event risk factor being determinable from one or more cardiac vector values selected from: sum magnitude of absolute QRST integral (SAI QRST), R/T peaks volume, spatial QRST angle, T-T' angles, R-R' angles, T-axes amplitudes, R-axes amplitudes, QRS loops areas, T loops areas, beat-to-beat variability in sum magnitude of absolute QRST integral (SAI QRST), beat-to-beat variability in R/T peaks volume, beat-to-beat variability in spatial QRST angle, beat-to-beat variability in T-T' angles, beat-to-beat variability in R-R' angles, beat-to-beat variability in T-axes amplitudes, beat-to-beat variability in R-axes amplitudes, beat-to-beat variability in QRS loops areas, and beat-to-beat variability in T loops areas wherein the ECG measurement equipment includes a surface ECG instrument and the ECG measurements are expressed as three lead orthogonal ECG data or the ECG measurement equipment includes an intracardiac electrogram instrument, and wherein the cardiac event risk factor is a SAI QRST that is determined by plotting a QRST curve for each lead of the expressed three lead orthogonal ECG data or for the ECG measurements, and calculated via the total sum of the absolute areas under the QRST curve for each of the three leads or the intracardiac electrogram instrument.

18. The ECG analysis system of claim 17, wherein the ECG measuring equipment includes the surface ECG instrument.

19. The ECG analysis system of claim 17, wherein the ECG measuring equipment includes the intracardiac electrogram instrument.

20. The ECG analysis system of claim 17, wherein the ECG analysis results include a cardiac event risk factor of low, intermediate, or high based upon the value of the at least one cardiac event risk factor.

21. A method for analyzing ECG measurements obtained from a patient to determine a patient risk factor corresponding to a level of risk of the patient experiencing a subsequent cardiac event, the method comprising the steps of:

(a) obtaining orthogonal ECG measurements of a patient with 3D ECG measuring equipment; and (b) providing the obtained ECG measurements to ECG analysis equipment that receives the ECG measurements, performs an ECG analysis, and provides ECG analysis results in a user readable format;

wherein the ECG analysis includes determining at least one cardiac event risk factor having a value, the at least one cardiac event risk factor being determinable from one or more cardiac vector values selected from: sum magnitude of absolute QRST integral (SAI QRST), R/T peaks volume, spatial QRST angle, T-T' angles, R-R' angles, T-axes amplitudes, R-axes amplitudes, QRS loops areas, T loops areas, beat-to-beat variability in sum magnitude of absolute QRST integral (SAI QRST), beat-to-beat variability in R/T peaks volume, beat-to-beat variability in spatial QRST angle, beat-to-beat variability in T-T' angles, beat-to-beat variability in R-R' angles, beat-to-beat variability in T-axes amplitudes, beat-to-beat variability in R-axes amplitudes, beat-to-beat variability in QRS loops areas, and beat-to-beat variability in T loops areas, and wherein the cardiac event risk factor is a low frequency SAI QRST determined by calculating the SAI QRST of orthogonal ECG measurements taken in the 10 Hz to 50 Hz band.

22. A method for analyzing ECG measurements obtained from a patient to determine a patient risk factor corresponding to a level of risk of the patient experiencing a subsequent cardiac event, the method comprising the steps of:

(a) obtaining ECG measurements of a patient with 3D ECG measuring equipment; and (b) providing the obtained ECG measurements to ECG analysis equipment that receives the ECG measurements, performs an ECG analysis, and provides ECG analysis results in a user readable format;

wherein the ECG analysis includes determining at least one cardiac event risk factor having a value, the at least one cardiac event risk factor being determinable from one or more cardiac vector values selected from: sum magnitude of absolute QRST integral (SAI QRST), R/T peaks volume, spatial QRST angle, T-T' angles, R-R' angles, T-axes amplitudes, R-axes amplitudes, QRS loops areas, T loops areas, beat-to-beat variability in sum magnitude of absolute QRST integral (SAI QRST), beat-to-beat variability in R/T peaks volume, beat-to-beat variability in spatial QRST angle, beat-to-beat variability in T-T' angles, beat-to-beat variability in R-R' angles, beat-to-beat variability in T-axes amplitudes, beat-to-beat variability in R-axes amplitudes, beat-to-beat variability in QRS loops areas, and beat-to-beat variability in T loops areas, wherein the ECG measurement equipment includes a surface ECG instrument or the ECG measurement equipment includes an intracardiac electrogram instrument, and wherein the cardiac event risk factor is a SAI QRST that is determined by plotting a QRST curve for the ECG data or for the ECG measurements, and calculated via the total sum of the absolute areas under the QRST curve.

* * * * *